United States Patent
Nakamura et al.

(10) Patent No.: US 7,115,734 B2
(45) Date of Patent: Oct. 3, 2006

(54) NUCLEIC ACID, NUCLEIC ACID FOR DETECTING DECHLORINATION BACTERIA, PROBE, METHOD FOR DETECTING DECHLORINATION BACTERIA AND METHOD FOR TREATING EARTH OR UNDERGROUND WATER POLLUTED BY CHLORINATED ETHYLENE OR CHLORINATED ETHANE

(75) Inventors: Kanji Nakamura, Atsugi (JP); Toshihiro Ueno, Atsugi (JP)

(73) Assignee: Kurita Water Industries Ltd., Tokyo (JP)

( * ) Notice: Subject to any disclaimer, the term of this patent is extended or adjusted under 35 U.S.C. 154(b) by 312 days.

(21) Appl. No.: 10/151,754

(22) Filed: May 15, 2002

(65) Prior Publication Data
US 2003/0165893 A1    Sep. 4, 2003

(30) Foreign Application Priority Data
May 18, 2001 (JP) ............................ 2001-149915
Jan. 30, 2002 (JP) ............................ 2002-021348

(51) Int. Cl.
*C07H 21/04* (2006.01)
*C12N 1/00* (2006.01)
*B09B 3/00* (2006.01)

(52) U.S. Cl. .................... 536/24.3; 435/243; 435/262.5
(58) Field of Classification Search ............... 536/24.3; 435/243, 262.5
See application file for complete search history.

(56) References Cited

U.S. PATENT DOCUMENTS 6,093,556 A    7/2000  Nakamura et al. .......... 435/167
6,797,817 B1 *  9/2004  Ebersole et al. ........... 536/24.3

FOREIGN PATENT DOCUMENTS

| EP | 0 864 542 | 9/1998 |
| WO | WO 96/27663 | 9/1996 |
| WO | WO 00/63443 | 10/2000 |

OTHER PUBLICATIONS

Trichloroethene Reductive Dehalogenase from *Dehalococcoides ethenogens*: Sequence of tceA and Substrate Range Characterization, by Jon K. Magnuson et al, Applied and Environmental Microbiology, vol. 66, No. 12, Dec. 2000, pp. 5141-5147.
Assessment of Indigenous Reductive Dechlorinating Potential at a TCE-Contaminated Site Using Microcosms, Polymerase Chain Reaction Analysis, and Site Data, by Donna E. Fennell et al, Environmental Science and Technology, vol. 35, No. 9, May 2001, pp. 1830-1839.,

* cited by examiner

*Primary Examiner*—Tekchand Saidha
(74) *Attorney, Agent, or Firm*—Flynn, Thiel, Boutell & Tanis, P.C.

(57) ABSTRACT

A nucleic acid composed of 17–30 nucleotides, which hybridizes with the DNA of dechlorination bacteria preferentially at the chlorinated ethylene-decomposing gene, or a nucleic acid composed of 10–50 nucleotides, which hybridizes with the DNA of dechlorination bacteria preferentially in a region containing the base sequence(s) characteristic to high performance dechlorination bacteria present upstream from the chlorinated ethylene-decomposing gene tceA, to be used for detecting selectively dechlorination bacteria, in particular high performance dechlorination bacteria, by performing a PCR using the nucleic acid mentioned above as the primer and the nucleic acid(s) in the sample bacteria as the template and detecting the thereby synthesized DNA fragments, in order to use the thus identified dechlorination bacteria for an efficient treatment of earth or underground waters polluted by chlorinated ethylene and/or chlorinated ethane.

2 Claims, 2 Drawing Sheets

NUCLEIC ACID, NUCLEIC ACID FOR DETECTING DECHLORINATION BACTERIA, PROBE, METHOD FOR DETECTING DECHLORINATION BACTERIA AND METHOD FOR TREATING EARTH OR UNDERGROUND WATER POLLUTED BY CHLORINATED ETHYLENE OR CHLORINATED ETHANE

FIELD OF THE INVENTION

The present invention relates to a nucleic acid which hybridizes with the DNA of dechlorination bacteria (bacteria decomposing chlorinated ethylene), preferentially at the chlorinated ethylene-decomposing gene or at a specific position upstream of the region of said gene; a labelled probe for detecting dechlorination bacteria constituted of the nucleic acid mentioned above; a method for detecting dechlorination bacteria using the nucleic acid or the labelled probe; and a method for treating earths or underground waters polluted by chlorinated ethylene and/or chlorinated ethane using the dechlorination bacteria detected thereby.

BACKGROUND OF THE INVENTION

There has been attempted a technique for decontaminating earth or underground water polluted by chlorinated ethylene or chlorinated ethane, wherein the chlorinated ethylene or chlorinated ethane is subjected to an anaerobic microbiological dechlorination (decomposition) using dechlorination bacteria existing originally in the polluted earth or underground water. For treating the polluted earth or underground water, it has been proposed to introduce such dechlorination bacteria into the polluted earth or underground water. It has been confirmed that such dechlorination bacteria can decompose not only chlorinated ethylene but also chlorinated ethane by means of a chlorinated ethylene-decomposing enzyme present in such dechlorination bacteria. Such a known technique may encounter a problem that it is not guaranteed that a better treating performance, namely, a complete dechlorination will always be attained.

For this reason, there has been a demand for an established method for discriminating preliminarily whether a contemplated dechlorination performance will be attained or not, in the case of treating earth or underground water polluted by chlorinated ethylene and/or chlorinated ethane using dechlorination bacteria. There is further a demand for a method for treating polluted earth or polluted underground water, in which the decontamination can be realized efficiently within a brief time in a reliable manner by utilizing a high performance dechlorination bacterium having a high dechlorination activity selected among the existing dechlorination bacteria.

SUMMARY OF THE INVENTION

An object of the present invention is to provide a novel and useful nucleic acid which can be used for detecting dechlorination bacteria, in particular, high performance dechlorination bacteria exhibiting high dechlorination activity and hybridizes with the DNA of dechlorination bacteria preferentially at the chlorinated ethylene-decomposing gene tceA or at a certain position in an upstream region adjoining the chlorinated ethylene-decomposing gene; a labelled probe for detecting dechlorination bacteria constituted of the above nucleic acid; a method for detecting dechlorination bacteria using the above nucleic acid or using the above labelled probe; and a method for treating earths or underground waters polluted by chlorinated ethylene and/or chlorinated ethane.

The present invention consists of the following nucleic acid, a labelled probe for detecting dechlorination bacteria constituted of the above nucleic acid, a method for detecting dechlorination bacteria using the above-mentioned nucleic acid or using the above labelled probe and a method for treating earth or underground water polluted by chlorinated ethylene and/or chlorinated ethane using the detected dechlorination bacterium:

(1) Nucleic acid which hybridizes with the DNA of dechlorination bacteria preferentially at the chlorinated ethylene-decomposing gene or at a position upstream thereof.

(2) The nucleic acid as defined in the above (1), which is composed of 17–30 nucleotides and hybridizes with the DNA of dechlorination bacteria preferentially at the chlorinated ethylene-decomposing gene, wherein the nucleic acid has any of base sequences of SEQ ID No. 1 through No. 46, any of base sequences having homologies of 90% or higher with respect to the base arrangements of the base sequences mentioned above or any of base sequences complementary to the afore- and above-mentioned base sequences.

(3) The nucleic acid as defined in the above (1), which is composed of 10–50 nucleotides and hybridizes with the DNA of dechlorination bacteria preferentially at the chlorinated ethylene-decomposing gene, wherein the nucleic acid includes, on the one hand, a base sequence of at least 10 succeeding nucleotides, which corresponds to a base sequence found in any of the base sequences of SEQ ID No. 1 through No. 46, or, on the other hand, a base sequence complementary to the afore-mentioned base sequence.

(4) The nucleic acid as defined in the above (1) selected from the following three kinds, namely, in the first place, the nucleic acid which is composed of 10–50 nucleotides and hybridizes with the DNA of dechlorination bacteria preferentially in a region adjoining the chlorinated ethylene-decomposing gene tceA upstream thereof of the DNA, which region consists of the base sequence shown by the sequence diagram (1) given below, wherein the hybridization is effected preferentially in such a range that includes at least one base disposed at the position indicated by the upward arrow (↑) or, in case the position indicated by the upward arrow (↑) is a base-defective position, in such a range that includes at least one pair of the bases adjoining the base-defective position up- and downstream thereof; in the second place, the nucleic acid which has a homology of at least 90% with respect to the base arrangement of the above first nucleic acid; and, in the third place, the nucleic acid which has a base sequence complementary to the above first or second nucleic acid.

```
ATGTTTGAAA TTCCGCATTG CTATGGTTCC AATAAGTGTT ATTATACTCA TTAATGAGAG    60
  ↑        ↑↑      ↑

ATTTACATAC TCTTCCCCGT AGGTATTAAT TCTATCTTCC TGCTGCTTAA TGTTATTTAA   120
```

-continued

```
ATCCATATCA CGCTCGTTTC CCATTTTTTA CTCACGTCCC TCCCAATCTA ATTCTCCAAC 180

TAACTCGCTT TGTGACTATT ATATTCTAAT TTAATAAATT TTCAATAAAA GTTTTAGTAA 240
    ↑

ACTTTTAATA TTTTTTTTTC ATTCTTTCGT GGCACGTGCG CTTTCCAAAG TGCTATCTTC 300
          ↑                                 ↑

TACTTAACAA CCCTTCCC-T TAAGATAGCA T--CAAGGAG GCAGATTATG CGTA-TTGGC 360
    ↑          ↑      ↑  ↑↑ ↑     ↑↑           ↑↑        ↑↑ ↑

TTGCGGACTA CCGCATGACA GACGCCAAAG TGCGAAAAGC TTTTTTTAA- TGAGGTATTT 420
                                                ↑

TAAAAGT                                                           427
```

. . . Sequence Diagram (1)

(the above sequence diagram (1) shows the base sequence in the region upstream of the gene tceA of the DNA of dechlorination bacteria, wherein the upward arrow "↑" indicates the position at which the hybridization occurs preferentially and the hyphen "-" indicates the base-defective position.)

(5) The nucleic acid as defined in the above (1) selected from the following three kinds, namely, in the first place, the base sequence of the upper series of the sequence diagram (2) given below, wherein the hybridization is effected preferentially in such a range that the base sequence is different between the upper series and the lower series; in the second place, the nucleic acid which has a homology of at least 90% with respect to the base arrangement of the above first nucleic acid; and, in the third place, the nucleic acid which has a base sequence complementary to the above first or second nucleic acid.

```
ATGTTTGAAA TTCCGCATTG CTATGGTTCC AATAAGTGTT ATTATACTCA TTAATGAGAG 60

ATATTTGTAG TTTCGCATTG CTATGGTTCC AATAAGTGTT ATTATACTCA TTAATGAGAG 60
    ↑   ↑ ↑  ↑

ATTTACATAC TCTTCCCCGT AGGTATTAAT TCTATCTTCC TGCTGCTTAA TGTTATTTAA 120

ATTTACATAC TCTTCCCCGT AGGTATTAAT TCTATCTTCC TGCTGCTTAA TGTTATTTAA 120

ATCCATATCA CGCTCGTTTC CCATTTTTTA CTCACGTCCC TCCCAATCTA ATTCTCCAAC 180

ATCCATATCA CGCTCGTTTC CCATTTTTTA CTCACGTCCC TCCCAATCTA ATTCTCCAAC 180

TAACTCGCTT TGTGACTATT ATATTCTAAT TTAATAAATT TTCAATAAAA GTTTTAGTAA 240

TAACTCGTTT TGTGACTATT ATATTCTAAT TTAATAAATT TTCAATAAAA GTTTTAGTAA 240
       ↑

ACTTTTAATA TTTTTTTTTC ATTCTTTCGT GGCACGTGCG CTTTCCAAAG TGCTATCTTC 300

ACTTTTAATA TTGTTTTTTC ATTCTTTCGT GGCACGTGCG CTTTCCAAGG TGCTATCTTC 300
              ↑                                    ↑

TACTTAACAA CCCTTCCC-T TAAGATAGCA T--CAAGGAG GCAGATTATG CGTA-TTGGC 360

TACTTAACAA ACCTTCCCGT TGAGTAAACA TTTCAAGGAG GCATGTTATG GATACTTGGC 360
    ↑          ↑      ↑  ↑↑ ↑     ↑↑           ↑↑        ↑↑ ↑

TTGCGGACTA CCGCATGACA GACGCCAAAG TGCGAAAAGC TTTTTTTAA- TGAGGTATTT 420

TTGCGGACTA CCGCATGACA GACGCCAAAG TGCGAAAAGC TTTTTTTAAA TGAGGTATTT 420
                                                ↑

TAAAAGT                                                           427

TAAAAGT                                                           427
```

. . . Sequence Diagram (2)

nucleic acid which is composed of 10–50 nucleotides and hybridizes with the DNA of dechlorination bacteria preferentially in an upstream region adjoining the chlorinated ethylene-decomposing gene tceA, which region consists of (the above sequence diagram (2) shows the base sequences in the region upstream of the gene tceA of dechlorination bacteria of two different strains by the upper and lower series thereof, respectively, in comparison of correspondence ther ebetween, wherein the upward arrow "↑" indicates the position at which the base is different between the upper and lower series and the hyphen "-" indicates the base-defective position.)

(6) The nucleic acid as defined in the above (1) selected from the following three kinds, namely, in the first place, the nucleic acid which is composed of 10–50 nucleotides and hybridizes with the DNA of dechlorination bacteria preferentially in an upstream region adjoining the chlorinated ethylene-decomposing gene tceA, which region consists of the base sequence of the upper series of the sequence diagram (2) given below, wherein the hybridization is effected preferentially in such a range that includes at least one base which is different from that present at the corresponding position in the lower series or, in case the base sequence is different between the upper series and the lower series due to absence of one or more bases in the upper series, in such a range that includes at least one pair of the bases adjoining the base-defective position up- and downstream thereof; in the second place, the nucleic acid which has a homology of at least 90% with respect to the base arrangement of the above first nucleic acid; and, in the third place, the nucleic acid which has a base sequence complementary to the above first or second nucleic acid.

(7) The nucleic acid as defined in the above (1), which is composed of 20–30 nucleotides and hybridizes with the DNA of dechlorination bacteria preferentially in the upstream region from the 1st to the 500th base from the chlorinated ethylene-decomposing gene tceA, wherein the nucleic acid has any of base sequences of SEQ ID No. 50 through No. 56, any of base sequences each having a homology of at least 90% with respect to the base arrangement of corresponding one of the above-mentioned base sequences or any of base sequences complementary to the afore- and above-mentioned base sequences.

(8) The nucleic acid as defined in the above (1) selected from the following two kinds, namely, on the one hand, nucleic acids each of which is composed of 10–50 nucleotides and hybridizes with the DNA of dechlorination bacteria preferentially in the upstream region from the 1st to the 500th base of the chlorinated ethylene-decomposing gene tceA, wherein the nucleic acids includes each a base sequence of at least 10 succeeding nucleotides, which base sequence is found in any of base sequences of SEQ ID No. 50 through No. 56 but not found in the base sequences of SEQ ID No. 57 through No. 63, and, on the other hand, nucleic acids

```
ATGTTTGAAA TTCCGCATTG CTATGGTTCC AATAAGTGTT ATTATACTCA TTAATGAGAG  60

ATATTTGTAG TTTCGCATTG CTATGGTTCC AATAAGTGTT ATTATACTCA TTAATGAGAG  60
  ↑   ↑↑  ↑

ATTTACATAC TCTTCCCCGT AGGTATTAAT TCTATCTTCC TGCTGCTTAA TGTTATTTAA 120

ATTTACATAC TCTTCCCCGT AGGTATTAAT TCTATCTTCC TGCTGCTTAA TGTTATTTAA 120

ATCCATATCA CGCTCGTTTC CCATTTTTTA CTCACGTCCC TCCCAATCTA ATTCTCCAAC 180

ATCCATATCA CGCTCGTTTC CCATTTTTTA CTCACGTCCC TCCCAATCTA ATTCTCCAAC 180

TAACTCGCTT TGTGACTATT ATATTCTAAT TTAATAAATT TTCAATAAAA GTTTTAGTAA 240

TAACTCGTTT TGTGACTATT ATATTCTAAT TTAATAAATT TTCAATAAAA GTTTTAGTAA 240
       ↑

ACTTTTAATA TTTTTTTTTC ATTCTTTCGT GGCACGTGCG CTTTCCAAAG TGCTATCTTC 300

ACTTTTAATA TTGTTTTTTC ATTCTTTCGT GGCACGTGCG CTTTCCAAGG TGCTATCTTC 300
          ↑                                           ↑

TACTTAACAA CCCTTCCC-T TAAGATAGCA T--CAAGGAG GCAGATTATG CGTA-TTGGC 360

TACTTAACAA ACCTTCCCGT TGAGTAAACA TTTCAAGGAG GCATGTTATG GATACTTGGC 360
          ↑        ↑ ↑ ↑↑ ↑    ↑↑          ↑↑         ↑↑  ↑

TTGCGGACTA CCGCATGACA GACGCCAAAG TGCGAAAAGC TTTTTTTAA- TGAGGTATTT 420

TTGCGGACTA CCGCATGACA GACGCCAAAG TGCGAAAAGC TTTTTTTAAA TGAGGTATTT 420
                                                     ↑

TAAAAGT                                                          427

TAAAAGT                                                          427
```

. . . Sequence Diagram (2)

(the above sequence diagram (2) shows the base sequences in the region upstream of the gene tceA of the dechlorination bacteria of two different strains by the upper and lower series thereof, respectively, in comparison of correspondence therebetween, wherein the upward arrow "↑" indicates the position at which the base is different between the upper and lower series and the hyphen "-" indicates the base-defective position.)

having base sequences complementary to the afore-mentioned nucleic acids.

(9) The nucleic acid as defined in any one of the preceding (1)–(8), wherein the nucleic acid is assigned for detecting dechlorination bacteria.

(10) A labelled probe for detecting dechlorination bacteria, comprising a nucleic acid as defined in any one of the preceding items, which nucleic acid is labelled by any of labelling means including radioactive elements, enzymes, fluorescent substances, antigens, antibodies and chemical substances.

(11) A method for detecting dechlorination bacteria, comprising
performing a PCR (polymerase chain reaction) using the nucleic acid as defined in any one of the above (1) to (9) for the primer and the nucleic acid(s) present in the sample bacterium for the template and
detecting the synthesized DNA fragments.

(12) A method for detecting dechlorination bacteria, comprising
bringing the labelled probe for detecting dechlorination bacteria as defined in the above (10) into contact with a sample bacterium or with nucleic acid(s) prepared from such sample bacterium to effect an RNA- or DNA-hybridization and
detecting the label of the probe.

(13) A method for treating earth or underground water polluted by chlorinated ethylene and/or chlorinated ethane using dechlorination bacteria, comprising
performing the method for detecting dechlorination bacteria as defined in the above (11) or (12) for samples of soil or underground water from various origins to identify a soil or underground water containing a dechlorination bacterium detected and
introducing the so-identified soil or underground water containing the dechlorination bacterium or a cultivation liquor inoculated with the identified soil or underground water into the earth or underground water polluted by chlorinated ethylene and/or chlorinated ethane.

DETAILED DESCRIPTION OF THE INVENTION

Figure 1:
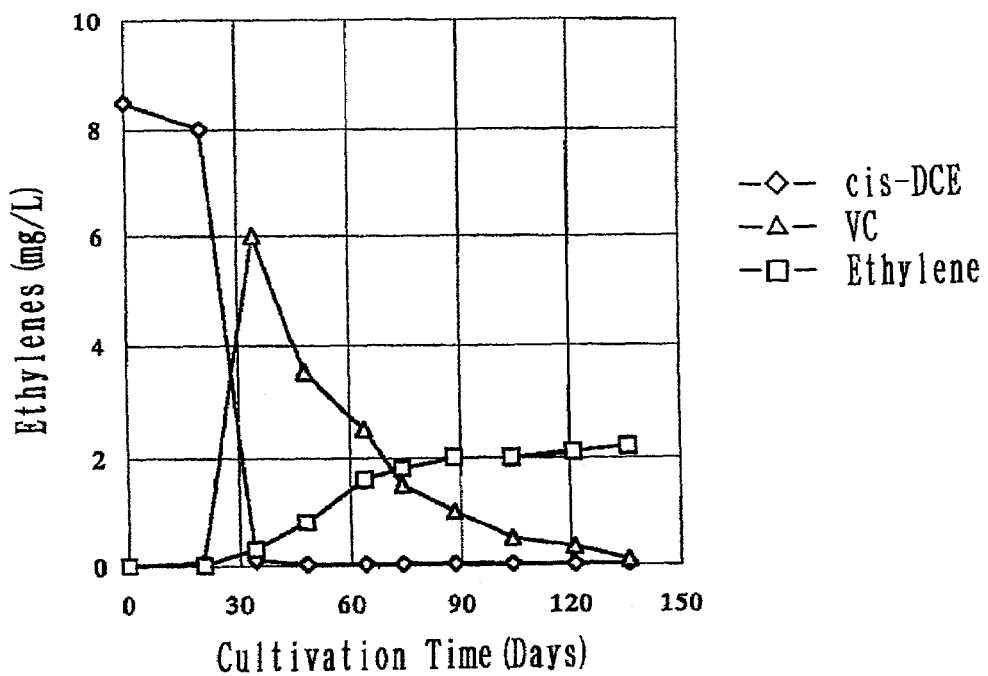
FIG. 1 is a graph showing the experimental results of Example 1-2.

The inventors had been in sound researches in decontamination treatment of earth or underground water polluted by chlorinated ethylene and/or chlorinated ethane using dechlorination bacteria in order to clarify the reason why the resulting treatment results attained are not always better, wherefrom the inventors obtained a knowledge that better treatment performance is attained when the earth or underground water to be treated contains original dechlorination bacteria living or growing there but may not be expected to attain better performance when there are no such living dechlorination bacteria.

It was further recognized by the inventors that there are cases where the dechlorination proceeds efficiently and where the dechlorination proceeds only slowly with accompaniment of accumulation of, in particular, vinyl chloride, even if the earth or underground water to be treated contains living dechlorination bacteria and the dechlorination bacteria have tceA gene which synthesizes decomposing enzyme identical with that originated from the externally incorporated dechlorination bacteria. By the researches of the inventors, it has been found that the above phenomenon is derived from the difference of base sequences in the upstream region adjoining the chlorinated ethylene-decomposing gene tceA. Namely, the microbiological decomposition of chlorinated ethylene by dechlorination bacteria proceeds in the succession of tetrachloroethylene→trichloroethylene→dichloroethylene→vinyl chloride→ethylene, in which the decomposition of vinyl chloride to ethylene proceeds at lower velocity and, therefore, vinyl chloride will accumulate.

Therefore, it may be possible to judge whether a microbiological dechlorination treatment of an earth or underground water can efficiently be realized or not, if living or growing dechlorination bacteria existing originally in such earth or underground water are detected on inspection thereof.

In particular, it may be possible to judge whether a microbiological dechlorination treatment of an earth or underground water can more efficiently and reliably be realized within a brief time or not, if living or growing dechlorination bacteria existing originally in such earth or underground water, which have high rate of dechlorination and high dechlorination activity (decomposing activity) and which show no accumulation of vinyl chloride, are detected on inspection thereof.

Dechlorination bacteria, especially those having high dechlorination activities, can be detected by utilizing the nucleic acid according to the present invention, whereby the above-mentioned judgment can be attained.

<<Nucleic acids which hybridize with the DNAs of dechlorination bacteria preferentially at the chlorinated ethylene-decomposing gene>>

In the context of this specification, the nucleic acids which hybridize with the DNAs of dechlorination bacteria preferentially at the chlorinated ethylene-decomposing gene are called, in some cases, "the first group nucleic acids".

In one aspect of the present invention, the first group nucleic acids according to the present invention are those which are composed of 17–30 nucleotides and hybridize with the DNA of dechlorination bacteria preferentially at the chlorinated ethylene-decomposing gene that codes the chlorinated ethylene-decomposing enzyme of the dechlorination bacteria, wherein each of the first group nucleic acids takes dechlorination bacteria as the target bacteria and has any of the base sequences SEQ ID No. 1 through No. 46 given in the SEQUENCE LISTING which appears afterwards, any of base sequences having a homology of at least 90% with respect to the base arrangement of any of the base sequences mentioned above or any of base sequences complementary to the afore- and above-mentioned base sequences.

In another aspect of the present invention, the first group nucleic acids according to the present invention are those which are composed of 10–50 nucleotides, preferably 15–35 nucleotides, and hybridize with the DNA of dechlorination bacteria preferentially at the chlorinated ethylene-decomposing gene that codes the chlorinated ethylene-decomposing enzyme of the dechlorination bacteria, wherein each of the first group nucleic acids includes, on the one hand, a base sequence composed of at least 10 succeeding nucleotides, which corresponds to a base sequence found in any of the base sequences of SEQ ID No. 1 through No. 46, or, on the other hand, a base sequence complementary to the aforementioned base sequence. Namely, the nucleic acid includes, for example, a base sequence which is the same as that composed of 10 or more succeeding bases found in the base sequence SEQ ID No. 1 starting from any arbitrary position of SEQ ID No. 1 and, thus, one or more bases may be present upstream and/or downstream of such base sequence of 10 or more succeeding bases.

The first group nucleic acids according to the present invention, namely, those which have any of the base sequences SEQ ID No. 1 through No. 46 of SEQUENCE LISTING given afterwards; any of base sequences each having a homology of at least 90% with respect to the base arrangement of any of the base sequences mentioned above; any of base sequences complementary to the afore- and above-mentioned base sequences; or any of base sequences including, on the one hand, a base sequence composed of at least 10 succeeding nucleotides, which corresponds to a base sequence found in any of the base sequences of SEQ ID No. 1 through No. 46, or, on the other hand, a base sequence complementary to the afore-mentioned base sequence, can be synthesized easily by known techniques in a chemical way.

The first group nucleic acids according to the present invention are designed in such a way that the base sequence of the chlorinated ethylene-decomposing gene of dechlorination bacteria is identified as shown by SEQ ID No. 47 of SEQUENCE LISTING given afterwards and utilizing segments thereof specific thereto, whereby the first group nucleic acids hybridize with the DNA of the dechlorination bacteria preferentially at the chlorinated ethylene-decomposing gene thereof. The chlorinated ethylene-decomposing gene represented by SEQ ID No. 47 is identical with the tceA gene described afterwards.

Specific examples of the dechlorination bacteria include those which belong to genera of Dehalococcoides and so on.

Specific examples of chlorinated ethylene subject to microbiological decomposition (dechlorination) by dechlorination bacteria include tetrachloro-ethylene (PCE), trichloroethylene (TCE), cis-1,2-dichloroethylene, trans-1,2-dichloroethylene, 1,1-dichloroethylene, vinyl chloride (VC) and dechlorination intermediates of them. Specific examples of chlorinated ethane subject to microbiological decomposition (dechlorination) include 1,2-dichloroethane and monochloroethane.

The first group nucleic acids according to the present invention can be used for easy and accurate and specifically identifiable detection of dechlorination bacteria by performing hybridization or PCR (polymerase chain reaction) using these nucleic acids as a primer, as will be detailed afterwards.

<<Nucleic acids which hybridize with the DNAs of dechlorination bacteria preferentially at a specific position in a region upstream of the chlorinated ethylene-decomposing gene>>

In the context of this specification, the nucleic acids which hybridize with the DNAs of dechlorination bacteria preferentially at a specific position in a region upstream of the chlorinated ethylene-decomposing gene are called, in some cases, "the second group nucleic acids". When designated simply as nucleic acids, this means nucleic acids of the first and/or the second group.

The inventors identified a high performance dechlorination bacterium, in particular, a high performance dechlorination bacterium exhibiting a high activity for decomposing vinyl chloride, among the detected dechlorination bacteria, and have determined the base sequence of the DNA region from the 1st to 500th base upstream of the chlorinated ethylene-decomposing gene tceA of the high performance dechlorination bacterium. The base sequence of the above DNA region upstream of the high performance chlorinated ethylene-decomposing gene is represented by the sequence diagram (1), by the upper series of the sequence diagram (2) given previously, by the upper series of the sequence diagram (3) given below and by SEQ ID No. 64 of SEQUENCE LISTING given afterwards. The inventors have determined also the base sequence of the DNA region from the 1st to 500th base upstream of the chlorinated ethylene-decomposing gene tceA of a dechlorination bacterium exhibiting a lower activity for decomposing vinyl chloride. The base sequence of the DNA region upstream of the chlorinated ethylene-decomposing gene of this dechlorination bacterium is represented by the lower series of the sequence diagram (2) given above, by the lower series of the sequence diagram (3) given below and by SEQ ID No. 65 of SEQUENCE LISTING given afterwards. In the sequence diagrams (2) and (3), the base sequences of the DNA region upstream of the chlorinated ethylene-decomposing gene of the high performance dechlorination bacterium and of the lower performance dechlorination bacterium are given in the upper series and in the lower series, respectively, for the sake of comparison.

The second group nucleic acids according to the present invention hybridize with the DNAs of high performance dechlorination bacteria preferentially at a specific position in a region adjoining the chlorinated ethylene-decomposing gene tceA upstream thereof, wherein the specific position should be in such a range that the base sequence of the DNA is different between the high performance dechlorination bacteria and the low activity dechlorination bacteria.

Thus, in one aspect of the present invention, the second group nucleic acids according to the present invention are selected from the following three kinds, namely, in the first place, a nucleic acid which is composed of 10–50 nucleotides and hybridizes with the DNA of dechlorination bacteria preferentially in an upstream region adjoining the chlorinated ethylene-decomposing gene tceA, which region consists of the base sequence shown by the sequence diagram (1) given above, wherein the hybridization is effected preferentially in such a range that includes at least one base disposed at the position indicated by the upward arrow (↑) or, in case the position indicated by the upward arrow (↑) is a base-defective position, in such a range that includes at least one pair of the bases adjoining the base-defective position up- and downstream thereof; in the second place, a nucleic acid which has a homology of at least 90% with respect to the base arrangement of the above first nucleic acid; and, in the third place, a nucleic acid which has a base sequence complementary to the above first or second nucleic acid.

In another aspect of the present invention, the second group nucleic acids according to the present invention are selected from the following three kinds, namely, in the first place, a nucleic acid which is composed of 10–50 nucleotides and hybridizes with the DNA of dechlorination bacteria preferentially in a region adjoining the chlorinated ethylene-decomposing gene tceA upstream thereof, which region consists of the base sequence of the upper series of the sequence diagram (2) given above, wherein the hybridization is effected preferentially in such a range that the base sequence is different between the upper series and the lower series; in the second place, a nucleic acid which has a homology of at least 90% with respect to the base arrangement of the above first nucleic acid; and, in the third place, a nucleic acid which has a base sequence complementary to the above first or second nucleic acid.

As the range in which the base sequence is different between the upper series and the lower series, there may be recited, for example, a range which includes at least one base which is different from that present at the corresponding position in the lower series or, in case the base sequence is different between the upper series and the lower series due to absence of one or more bases in the upper series, a range that includes at least one pair of the bases adjoining the base-defective position up- and downstream thereof.

In a further aspect of the present invention, the second group nucleic acids according to the present invention are each composed of 20–30 nucleotides and hybridize with the DNA of dechlorination bacteria preferentially in the region of the 1st –500th base from the chlorinated ethylene-decomposing gene tceA upstream thereof, wherein each of the nucleic acids has any of the base sequences of SEQ ID No. 50 through No. 56 of SEQUENCE LISTING, any of base sequences each having a homology of 90% or higher with respect to the base arrangement of corresponding ones of the above-mentioned base sequences or any of base sequences complementary to the afore- and above-mentioned base sequences.

The sequence diagram (3) given below shows, in what range in the region upstream of the gene tceA each of the base sequences SEQ ID No. 50 through No. 56 is found. The base sequence from 1st to 427th base of the sequence diagram (3) is the same as that of sequence diagram (2).

The above sequence diagram (3) shows the base sequences in the region upstream of the gene tceA of each DNA of dechlorination bacteria of two different strains by the upper and lower series thereof, respectively, in comparison of correspondence therebetween, wherein the upward arrow "↑" indicates the position at which the base is different between the upper and lower series and the hyphen "-" indicates the base-defective position and wherein VC1 to VC7 indicate each the base sequence of each of SEQ ID No. 50 to No. 56, respectively, the symbol "tceA" indicates a partial base sequence found in the gene tceA and the symbol "VCr1" indicates the primer used in the Examples.

As seen from the sequence diagram (3), the nucleic acids having the base sequences of SEQ ID No. 50 through No. 56 (VC1 to VC7) hybridize in such ranges where the base sequence is different between the upper series and the lower series of the sequence diagram (2), namely, in characteristic ranges for the high performance dechlorination bacterium. By the way, it is to be noted that, while there is a difference between the upper and lower series base sequences at the 478th and 479th bases in the sequence diagram (3), the amino acid assigned for the base sequence in this range is the same for the upper and lower series nucleic acids and, thus,

```
←-------VC1-------→
ATGTTTGAAA TTCCGCATTG CTATGGTTCC AATAAGTGTT ATTATACTCA TTAATGAGAG  60

ATATTTGTAG TTTCGCATTG CTATGGTTCC AATAAGTGTT ATTATACTCA TTAATGAGAG  60
  ↑    ↑ ↑   ↑

ATTTACATAC TCTTCCCCGT AGGTATTAAT TCTATCTTCC TGCTGCTTAA TGTTATTTAA  120

ATTTACATAC TCTTCCCCGT AGGTATTAAT TCTATCTTCC TGCTGCTTAA TGTTATTTAA  120

←--VC2-
ATCCATATCA CGCTCGTTTC CCATTTTTTA CTCACGTCCC TCCCAATCTA ATTCTCCAAC  180

ATCCATATCA CGCTCGTTTC CCATTTTTTA CTCACGTCCC TCCCAATCTA ATTCTCCAAC  180

---------------------→                      ←---
TAACTCGCTT TGTGACTATT ATATTCTAAT TTAATAAATT TTCAATAAAA GTTTTAGTAA  240

TAACTCGTTT TGTGACTATT ATATTCTAAT TTAATAAATT TTCAATAAAA GTTTTAGTAA  240
       ↑

-----------VC3-------------→         ←--------VC4-------
ACTTTTAATA TTTTTTTTTC ATTCTTTCGT GGCACGTGCG CTTTCCAAAG TGCTATCTTC  300

ACTTTTAATA TTGTTTTTTC ATTCTTTCGT GGCACGTGCG CTTTCCAAGG TGCTATCTTC  300
            ↑                                     ↑

-----------→←-------VC5    -------→←-----------VC6-----------
TACTTAACAA CCCTTCCC-T TAAGATAGCA T--CAAGGAG GCAGATTATG CGTA-TTGGC  360

TACTTAACAA ACCTTCCCGT TGAGTAAACA TTTCAAGGAG GCATGTTATG GATACTTGGC  360
        ↑        ↑  ↑ ↑  ↑↑ ↑   ↑↑          ↑↑       ↑↑ ↑

----→        ←----- -------VC7-----------
TTGCGGACTA CCGCATGACA GACGCCAAAG TGCGAAAAGC TTTTTTTAA- TGAGGTATTT  420

TTGCGGACTA CCGCATGACA GACGCCAAAG TGCGAAAAGC TTTTTTTAAA TGAGGTATTT  420
                                                   ↑

--→    ←--tceA--       ←-------VCr1-------→
TAAAAGTATG AGTGAAAAAT ATCATTCTAC AGTCACAAGG CGTGATTTCA TGAAGAGGCT  480

TAAAAGTATG AGTGAAAAAT ATCATTCTAC AGTCACAAGG CGTGATTTCA TGAAGAGATT  480

AGGTTTGGCA GGAGCCGGTG                                             500

AGGTTTGGCA GGAGCCGGTG                                             500
```

. . . Sequence Diagram (3)

no difference exists in the amino acid sequence between the decomposition enzymes expressed from them.

The second group nucleic acids according to the present invention are those which are selected from the following two kinds, namely, on the one hand, nucleic acids each of which is composed of 10–50 nucleotides, preferably 15–35 nucleotides, and hybridizes with the DNA of dechlorination bacteria preferentially in the region adjoining the chlorinated ethylene-decomposing gene tceA from the 1st to the 500th base upstream of the said gene, wherein the said nucleic acids includes each a base sequence of at least 10 succeeding nucleotides, which base sequence is found in any of base sequences of SEQ ID No. 50 through No. 56 but not found in the base sequences of SEQ ID No. 57 through No. 63, and, on the other hand, nucleic acids having base sequences complementary to the afore-mentioned nucleic acids. For such nucleic acids, there may be exemplified those given below. Thus, there may be recited, for example, nucleic acids having a base sequence identical with a base sequence of at least 10 succeeding bases, which is found in SEQ ID No. 50 at a position starting from any arbitrary site thereof but which is not found in any of the seven base sequences SEQ ID No. 57 through No. 63, namely, any base sequence of a corresponding number of bases chosen arbitrarily in any of SEQ ID No. 57 through No. 63 does not correspond to the said base sequence identical with that of said at least 10 succeeding bases; nucleic acids having base sequences complementary to those of above nucleic acids; and nucleic acids in which one or more bases are bound to the above-mentioned nucleic acids upstream and/or downstream thereof. The base sequences of SEQ ID No. 57 through No. 63 are those which correspond to the portions VC1 to VC7 in the lower series sequence of the sequence diagram (3), namely, that of the dechlorination bacterium of lower dechlorination activity.

The second group nucleic acids according to the present invention can easily be synthesized in a chemical way by a known technique.

The second group nucleic acids according to the present invention are designed in such a manner that a high performance dechlorination bacterium, in particular, a high performance dechlorination bacterium exhibiting high activity for decomposing vinyl chloride is first detected among dechlorination bacteria and the base sequence of the DNA of the so-detected bacterium in the region from the 1st to the 500th base upstream from the chlorinated ethylene-decomposing gene tceA of the DNA is determined, in order to utilize the characteristic portions of the so-determined base sequence, so that the second group nucleic acids according to the present invention hybridize with the DNA of the high performance dechlorination bacteria exhibiting especially high activity for decomposing vinyl chloride preferentially at specific sites in the region upstream of the gene tceA thereof.

Specific examples of the high performance dechlorination bacteria include those belonging to the genus Dehalococcoides and so on.

Specific examples of the chlorinated ethylene subject to decomposition (dechlorination) by dechlorination bacteria include tetrachloroethylene (PCE), trichloroethylene(TCE), cis-1,2-dichloroethylene, trans-1,2-dichloroethylene, 1,1-dichloroethylene, vinyl chloride(VC) and dechlorination intermediates of them. For specific examples of chlorinated ethane subject to decomposition (dechlorination) by dechlorination bacteria, there may be enumerated, for example, 1,2-dichloroethane and monochloroethane.

The chlorinated ethylene-decomposing gene tceA is included in the base sequence data of AF228507 registered in the GenBank of USA. In the context of this specification, "gene tceA" means not only that of the base sequence entered in the base sequence data of AF225807 but also one which has a homology of at least 90% of the gene arrangement of this gene.

The second group nucleic acids according to the present invention can be used for detecting high performance dechlorination bacteria, especially those exhibiting high activity of decomposing vinyl chloride, selectively in an easy manner with specifically high accuracy by carrying out a PCR (polymerase chain reaction) using the second group nucleic acid as the primer or by performing hybridization. Therefore, it is also possible, for example, to use the second group nucleic acid for judging whether the dechlorination bacterium having a chlorinated ethylene-decomposing gene under inspection is a high performance dechlorination bacterium or a lower performance dechlorination bacterium.

<<Labelled probe for detecting dechlorination bacteria>>

The labelled probe for detecting dechlorination bacteria according to the present invention consists of a nucleic acid of the first group or the second group labelled with a labelling means, such as a radioactive element, fluorescent substance, chemical material, antigen, antibody or enzyme. For such a labelling means, conventionally employed labelling materials can be used, among which there may specifically be recited, for example, radioactive elements, such as $^{32}P$ etc.; fluorescent substances, such as FITC (fluorescence isothiocyanate) and Rhodamines; haptens, such as digoxygenin etc.; enzymes, such as alkaline phosphatase, peroxidase and so on; and biochemical substances, such as biotin and so on. These labelling materials can be introduced into the nucleic acid by known techniques.

By using the dechlorination bacteria detecting probe according to the present invention, a dechlorination bacterium can be detected at a high accuracy in an easy manner, by inspecting a sample of bacterium by hybridizing it with the labelled probe, followed by detection of the labelling material in the dechlorination bacterium having the hybridized labelled probe by an adequate technique. In particular, the probe labelled with the nucleic acid of the second group according to the present invention can be used for detecting high performance dechlorination bacteria selectively.

<<Method for detecting dechlorination bacteria>>

The method for detecting dechlorination bacteria according to the present invention is based on detection using the nucleic acid according to the present invention. Thus, presence of a dechlorination bacterium in an inspection sample can be judged, when DNA of an expected size is synthesized on examination by PCR using any one of the nucleic acids according to the present invention as the primer and a nucleic acid prepared from the sample to be inspected as the template. Especially, when the examination is carried out using the second group nucleic acid according to the present invention, high performance dechlorination bacteria can be detected selectively.

PCR can be performed in a manner known per se, wherein use of a commercial kit for PCR may be permissible. For performing PCR, two primers, namely, an upper primer and a lower primer, are usually incorporated, wherein it is permissible to use the nucleic acids according to the present invention as either one or both of these primers. By performing a plurality of PCRs using a plurality of different nucleic acids as the primer, the reliability of detection can be increased.

The method for detecting dechlorination bacteria according to the present invention is based on the use of the labelled probe for detecting dechlorination bacteria according to the present invention. Thus, the method is performed in such a way that the labelled probe for detecting dechlorination bacteria according to the present invention is brought into contact with a sample containing bacteria to be inspected for the presence of dechlorination bacteria or with the nucleic acid(s) prepared from such sample to cause an RNA- or DNA-hybridization, whereupon the detection of the bacteria is effected by using the label as indicator. The hybridization can be carried out in a conventional way. Especially, when the detection is carried out using a probe labelled with a second group nucleic acid according to the present invention, high performance dechlorination bacteria can be detected selectively.

Detection of the dechlorination bacteria after the hybridization can be realized by a known technique in accordance with each specific labelling material employed. Thus, the detection may be realized for the case where a radioactive element is used for the label, by observing the radioactive ray by a known technique. When a fluorescent substance is used as the label, the detection can be attained by observing the fluorescent light by a known practice. When an enzyme is used as the label, the detection can be attained by determining the enzymatic activity. When a chemical substance is used as the label, the detection can be effected by analyzing the substance by a known method. When an antigen or an antibody is used as the label, the detection can be realized by carrying out an antigen-antibody reaction using an antibody or an antigen capable of reacting specifically with the labelled antigen or antibody and analyzing the resulting reaction product by known techniques.

If no dechlorination bacterium is detected by the method for detecting dechlorination bacteria according to the present invention using the first group nucleic acids according to the present invention, it is judged that dechlorination bacterium are absent. If no dechlorination bacteria are detected by the method using the second group nucleic acids according to the present invention, it is judged that there are no dechlorination bacteria in the examined sample or that the existing bacteria, if present, are those of lower decomposition activity.

By examining earth or underground water polluted by chlorinated ethylene and/or chlorinated ethane by the method for detecting dechlorination bacteria, especially for detecting high performance dechlorination bacteria, according to the present invention, it is possible to judge preliminarily whether or not the earth or underground water can reliably be dechlorinated efficiently within a brief time. It is also possible to take a pertinent measure for treating the polluted earth or underground water judged as devoid of dechlorination bacteria by, for example, introducing dechlorination bacterium, in particular, a high performance dechlorination bacterium, into such earth or underground water.

<<Method for treating earth or underground water polluted by chlorinated ethylene and/or chlorinated ethane>>

The method for treating earth or underground water polluted by chlorinated ethylene and/or chlorinated ethane according to the present invention comprises characteristic features of performing the above-mentioned method for detecting dechlorination bacteria according to the present invention for samples of underground waters and soils from various origins to identify underground water or soil containing a dechlorination bacterium and introducing the so-identified underground water or soil containing the dechlorination bacterium or a cultivation liquor inoculated with the identified underground water or soil (each referred to hereinafter sometimes as a bacterial dechlorination additive) into the earth or underground water polluted by chlorinated ethylene and/or chlorinated ethane (referred to hereinafter sometimes as the polluted environment). By performing the method for detecting dechlorination bacteria according to the present invention using the second group nucleic acid and utilizing the thereby obtained high performance bacterial dechlorination additive, the polluted environment can efficiently be treated (decontaminated).

The bacterial dechlorination additive to be introduced into the polluted environment may be any of those detected (collected) at any place. For example, underground water or soil, which has been collected from a place not polluted by chlorinated ethylene or chlorinated ethane but in which a dechlorination bacterium has been detected, or a cultivation liquor inoculated with such underground water or soil containing the detected dechlorination bacterium may be introduced into the underground water or earth polluted by chlorinated ethylene and/or chlorinated ethane to attain thereby treatment of the polluted underground water or earth. It is possible also to perform in such a way that underground water or soil, which has been collected from a place polluted by chlorinated ethylene and/or chlorinated ethane and in which a dechlorination bacterium has been detected, or a cultivation liquor inoculated with such underground water or soil containing the detected dechlorination bacterium is introduced into the ground of the above-mentioned polluted place or into the ground of another place, in order to cause thereby treatment of underground water or earth polluted by chlorinated ethylene and/or chlorinated ethane.

For performing the introduction of the bacterial dechlorination additive into the polluted environment, there may practically be employed, for example, a method in which the bacterial dechlorination additive is sprayed over the earth surface of the polluted area or a method in which the bacterial dechlorination additive is injected through a pipe (injection well) into the underground earth at the source of the underground water. The injection may be effected not only at the polluted place but also at a place upstream of the underground water.

Treatment of earth or underground water polluted by chlorinated ethylene and/or chlorinated ethane by the method according to the present invention may be attained, in possible cases, by introducing only the soil or underground water containing living dechlorination bacteria as detected or a cultivation liquor inoculated therewith into the polluted environment, though it may in some cases be worthwhile to further introduce additional water, nutrient matter and so on. When sufficient treatment of the polluted earth or underground water is not attainable by a single dose of the bacterial dechlorination additive, it may be possible to perform several repeats of doses of the bacterial dechlorination additive. It may further be permitted to take such a measure that the bacterial dechlorination additive is coagulated by adding thereto a coagulating agent or that the bacterial dechlorination additive is adsorbed on a carrier and the resulting carrier having thereon the adsorbed bacterial dechlorination additive is introduced into the polluted environment.

By treating the earth or underground water polluted by chlorinated ethylene and/or chlorinated ethane by microbiological decomposition as described above, the polluted environment polluted by chlorinated ethylene and/or chlorinated ethane can reliably be decontaminated, wherein an efficient and reliable treatment can be attained within a brief time without any accumulation of vinyl chloride by using, in particular, high performance dechlorination bacteria.

As described above, the first group and second group nucleic acids according to the present invention are novel and useful.

The first group nucleic acids according to the present invention have a specific base sequence and hybridize with the DNA of dechlorination bacteria preferentially at the chlorinated ethylene-decomposing gene and, therefore, they can be used for detecting dechlorination bacteria.

The second group nucleic acids according to the present invention hybridize with the DNA of high performance dechlorination bacteria preferentially at specific positions in the region adjoining the chlorinated ethylene-decomposing gene tceA upstream thereof of the high performance dechlorination bacteria and, therefore, they can be used for detecting high performance dechlorination bacteria selectively.

The nucleic acid for detecting dechlorination bacteria according to the present invention is constituted of one of the first group nucleic acids or of the second group nucleic acids as mentioned above and, therefore, dechlorination bacteria, especially high performance dechlorination bacteria can specifically and easily be detected at a high reliability by using the nucleic acid.

The labelled probe for detecting dechlorination bacteria according to the present invention is prepared by labelling one of the first group nucleic acids or the second group nucleic acids mentioned above and, therefore, can be used for detecting dechlorination bacteria, in particular, high performance dechlorination bacteria specifically and easily at a high reliability by utilizing the label as the detectable indicator.

The method for detecting dechlorination bacteria according to the present invention utilizes a nucleic acid selected among the above-mentioned first group and second group nucleic acids or the labelled probe and, therefore, can be used for detecting dechlorination bacteria, in particular, high performance dechlorination bacteria specifically and easily at a high reliability.

The method for treating earth or underground water polluted by chlorinated ethylene and/or chlorinated ethane according to the present invention can afford the decontamination of polluted earth or underground water by introducing underground water or earth, in which a dechlorination bacterium, in particular, a high performance dechlorination bacterium has been detected by the above-mentioned detecting method, or a cultivation liquor inoculated with the detected bacterium, into the polluted earth or underground water and, therefore, can treat such polluted earth or underground water efficiently and easily in an reliable way within a brief time to thereby decontaminate the polluted environment.

THE BEST MODE FOR EMBODYING THE INVENTION

In the following, the present invention will further be described in more detail by way of embodiments.

REFERENCE EXAMPLE 1-1

DNAs were extracted from eight underground waters from eight polluted areas where microbiological decomposition of chlorinated ethylene had been confirmed, whereupon PCR synthesis of DNA fragments including the entire range of the chlorinated ethylene-decomposing gene was performed. The primer pair used here (5'-TAACCT-TCTAAAACATCCTG-3' (SEQ ID No. 48) and 5'-GCAC-CACCCATAATAATCTA-3'(SEQ ID No. 49)) were designed from the base sequence data of AF228507 registered in the GenBank in USA, wherein an adjoining region of the chlorinated ethylene-decomposing gene was utilized. The base sequence data of AF228507 include the chlorinated ethylene-decomposing gene tceA registered.

By PCR synthesis, clones which have high homologies with respect to the base arrangement of the chlorinated ethylene-decomposing gene tceA were obtained from four underground waters, of which base sequences were determined. The base sequence of the chlorinated ethylene-decomposing gene was the same for all the four underground water samples and had a homology of 96% with respect to the reported base arrangement of the gene tceA. The determined entire base sequence of the chlorinated ethylene-decomposing gene is recited in SEQ ID No. 47 in the SEQUENCE LISTING.

EXAMPLE 1-1

Samples of underground waters were collected from the three points A, B and C, where dechlorination of chlorinated ethylene and/or chlorinated ethane (referred to as "ethylenization") was occurring, and from the three other points D, E and F, where ethylenization was not occurring, whereupon DNAs were extracted from each 100 ml of these samples in the manner as given below:

(1) Extraction of DNA

Each 100 ml of each underground water were filtered through a filter of a pore size of 0.2 µm and were stored in a tube of a capacity of 2 ml. To the tube were added then 1 ml of zirconia/silica beads of 0.1 mm bead size and 1 ml of an extraction buffer {100 mM Tris-HCl (pH=8.0), 100 mM sodium EDTA (pH=8.0), 100 mM sodium phosphate (pH=8.0) and 1.5 M NaCl}, whereupon the mixture was treated on a cell crusher "Bead Beater" for 2 minutes. The so-treated mixture was then subjected to three repeats of freezing/thawing and, then, 10 µl of proteinase K (10 mg/ml) were added to the mixture and the resulting mixture was held at 37° C. thermostatically for 30 minutes. To this mixture were then added 250 µl of 10% SDS solution and the resulting mixture was held thermostatically at 65° C. for two hours, whereupon the mixture was subjected again to the above-mentioned Bead Beater treatment. Then, the treated mixture was centrifugated at 8000×g for 10 minutes at room temperature and the resulting supernatant was collected. The supernatant was treated with chloroform to remove contamination proteins, whereupon the separated upper aqueous layer was isolated and processed by addition of an equivolume of isopropanol, allowed to stand for 60 minutes at room temperature and centrifugation at 8000×g for 20 minutes at room temperature to precipitate the DNA. The resulting precipitate was washed with 70% ethanol and then dried, before it was re-dissolved in 50 µl of sterile distilled water.

Using this extracted DNA solution, PCR was performed in the manner as described below, in order to examine whether or not dechlorination bacterium was present.

(2) Amplification of chlorinated ethylene-decomposing gene by PCR

Using 1 µl of the extracted DNA solution obtained in the above (1) as the template, the region of the chlorinated ethylene-decomposing gene was amplified by PCR. The volume of the reaction liquor of PCR-amplification was supplemented to 100 µl and there were used 2.5 U of Ex Taq DNA polymerase (a product of Takara Shuzo Co., Ltd.) and 200 μM of dNTP. For the primer pair, each 20 pmol of each pair among the 46 sets of primer pairs given in Table 1 were used. For other components of the reaction liquor composition, the guides of the manual attached to the PCR kit were followed. The PCR was effected according to the steps which comprise pre-heating at 94° C. for 2 minutes, subsequent 30 cyclic repeats of the first step of 94° C. for 20 seconds, the second step of 55° C. for 30 seconds and the third step of 72° C. for two minutes, followed by a post-extension of 72° C. for 7 minutes.

Each 2 μl of the PCR reaction liquor were subjected to an agarose electrophoresis, wherein presence of a dechlorination bacterium was judged when a DNA fragment of expected size was synthesized. The results are recited in Table 1.

TABLE 1

| No. | Upper Primer | Lower Primer: nucleic acid complementary to | A | B | C | D | E | F |
|---|---|---|---|---|---|---|---|---|
| 1 | KWI-Dhalo 1 | KWI-Dhalo 30 | ○ | ○ | ○ | X | X | X |
| 2 | KWI-Dhalo 2 | KWI-Dhalo 30 | ○ | ○ | ○ | X | X | X |
| 3 | KWI-Dhalo 3 | KWI-Dhalo 31 | ○ | ○ | ○ | X | X | X |
| 4 | KWI-Dhalo 4 | KWI-Dhalo 30 | ○ | ○ | X | X | X | X |
| 5 | KWI-Dhalo 5 | KWI-Dhalo 30 | ○ | ○ | ○ | X | X | X |
| 6 | KWI-Dhalo 6 | KWI-Dhalo 30 | ○ | ○ | ○ | X | X | X |
| 7 | KWI-Dhalo 7 | KWI-Dhalo 30 | ○ | ○ | ○ | X | X | X |
| 8 | KWI-Dhalo 8 | KWI-Dhalo 31 | ○ | ○ | ○ | X | X | X |
| 9 | KWI-Dhalo 9 | KWI-Dhalo 30 | ○ | ○ | X | X | X | X |
| 10 | KWI-Dhalo 10 | KWI-Dhalo 42 | ○ | ○ | ○ | X | X | X |
| 11 | KWI-Dhalo 11 | KWI-Dhalo 41 | ○ | ○ | ○ | X | X | X |
| 12 | KWI-Dhalo 12 | KWI-Dhalo 41 | X | ○ | ○ | X | X | X |
| 13 | KWI-Dhalo 13 | KWI-Dhalo 41 | ○ | ○ | ○ | X | X | X |
| 14 | KWI-Dhalo 14 | KWI-Dhalo 41 | X | ○ | ○ | X | X | X |
| 15 | KWI-Dhalo 15 | KWI-Dhalo 42 | ○ | ○ | ○ | X | X | X |
| 16 | KWI-Dhalo 16 | KWI-Dhalo 42 | ○ | ○ | X | X | X | X |
| 17 | KWI-Dhalo 17 | KWI-Dhalo 42 | ○ | ○ | ○ | X | X | X |
| 18 | KWI-Dhalo 18 | KWI-Dhalo 41 | X | ○ | ○ | X | X | X |
| 19 | KWI-Dhalo 19 | KWI-Dhalo 41 | ○ | ○ | ○ | X | X | X |
| 20 | KWI-Dhalo 20 | KWI-Dhalo 41 | ○ | ○ | ○ | X | X | X |
| 21 | KWI-Dhalo 21 | KWI-Dhalo 41 | X | ○ | ○ | X | X | X |
| 22 | KWI-Dhalo 22 | KWI-Dhalo 41 | ○ | ○ | ○ | X | X | X |
| 23 | KWI-Dhalo 23 | KWI-Dhalo 41 | ○ | ○ | ○ | X | X | X |
| 24 | KWI-Dhalo 24 | KWI-Dhalo 42 | ○ | ○ | X | X | X | X |
| 25 | KWI-Dhalo 25 | KWI-Dhalo 41 | ○ | ○ | ○ | X | X | X |
| 26 | KWI-Dhalo 26 | KWI-Dhalo 41 | X | ○ | ○ | X | X | X |
| 27 | KWI-Dhalo 27 | KWI-Dhalo 44 | ○ | ○ | ○ | X | X | X |
| 28 | KWI-Dhalo 28 | KWI-Dhalo 41 | ○ | ○ | ○ | X | X | X |
| 29 | KWI-Dhalo 29 | KWI-Dhalo 41 | ○ | ○ | ○ | X | X | X |
| 30 | KWI-Dhalo 17 | KWI-Dhalo 30 | ○ | X | ○ | X | X | X |
| 31 | KWI-Dhalo 16 | KWI-Dhalo 31 | ○ | ○ | ○ | X | X | X |
| 32 | KWI-Dhalo 17 | KWI-Dhalo 32 | ○ | ○ | ○ | X | X | X |
| 33 | KWI-Dhalo 15 | KWI-Dhalo 33 | ○ | ○ | X | X | X | X |
| 34 | KWI-Dhalo 15 | KWI-Dhalo 34 | ○ | ○ | ○ | X | X | X |
| 35 | KWI-Dhalo 16 | KWI-Dhalo 35 | X | ○ | ○ | X | X | X |
| 36 | KWI-Dhalo 17 | KWI-Dhalo 36 | ○ | ○ | ○ | X | X | X |
| 37 | KWI-Dhalo 17 | KWI-Dhalo 37 | ○ | ○ | ○ | X | X | X |
| 38 | KWI-Dhalo 17 | KWI-Dhalo 38 | X | ○ | ○ | X | X | X |
| 39 | KWI-Dhalo 16 | KWI-Dhalo 39 | ○ | ○ | ○ | X | X | X |
| 40 | KWI-Dhalo 17 | KWI-Dhalo 40 | ○ | ○ | ○ | X | X | X |
| 41 | KWI-Dhalo 17 | KWI-Dhalo 41 | ○ | X | ○ | X | X | X |
| 42 | KWI-Dhalo 17 | KWI-Dhalo 42 | ○ | ○ | ○ | X | X | X |
| 43 | KWI-Dhalo 17 | KWI-Dhalo 43 | ○ | ○ | ○ | X | X | X |
| 44 | KWI-Dhalo 16 | KWI-Dhalo 44 | ○ | ○ | X | X | X | X |
| 45 | KWI-Dhalo 16 | KWI-Dhalo 45 | ○ | ○ | ○ | X | X | X |
| 46 | KWI-Dhalo 17 | KWI-Dhalo 46 | ○ | ○ | ○ | X | X | X |

Notes:
○ denotes the case where synthesis of DNA was observed.
X denotes the case where synthesis of DNA was not observed.

From the results of Table 1, it is seen that DNA synthesis was observed in almost all the cases for the samples of the points A, B and C where ethylenization was not observed, with exception without observed DNA synthesis of only 15 cases among 138 samples. In contrast thereto, no DNA synthesis was observed for the samples of the points D, E and F where no ethylenization was detected. From this, it was shown that dechlorination bacterium is present always at such a point where ethylenization occurs and that monitoring thereof can be attained.

The base sequences (from 5'-end to 3'-end) of KWI-Dhalo 1 to KWI-Dhalo 46 in Table 1 are as follows:

```
KWI-Dhalo 1:  SEQ ID No. 1:   GAGGCTAGGTTTGGCAG

KWI-Dhalo 2:  SEQ ID No. 2:   TTGCAGAGAATAACCTG

KWI-Dhalo 3:  SEQ ID No. 3:   TTAAAGATGTTGATGACCTGCTGTCAGCAG

KWI-Dhalo 4:  SEQ ID No. 4:   GTAAAGCTTTAGAGGGTGAC

KWI-Dhalo 5:  SEQ ID No. 5:   GGGTGACCACGCTAATAAAG

KWI-Dhalo 6:  SEQ ID No. 6:   TGAGCCATGGTGGGTTACCA

KWI-Dhalo 7:  SEQ ID No. 7:   TGAGGATCCAACCTGTAATA

KWI-Dhalo 8:  SEQ ID No. 8:   GCCTTATAAAAAGATACAGC

KWI-Dhalo 9:  SEQ ID No. 9:   TGGAACAACCAGGGAGCATA

KWI-Dhalo 10: SEQ ID No. 10:  CTTCTTACCTGAGGATTACC

KWI-Dhalo 11: SEQ ID No. 11:  TGTCTCCAACCTATACAGGT

KWI-Dhalo 12: SEQ ID No. 12:  ATACTGCGATAGTGCCTTTA

KWI-Dhalo 13: SEQ ID No. 13:  TAAAATCAGGCATAGACTGG
```

-continued

```
KWI-Dhalo 14: SEQ ID No. 14:    ATGAAGGAAAATATTGATCC
KWI-Dhalo 15: SEQ ID No. 15:    AGATTATGACCCTGGTGAAC
KWI-Dhalo 16: SEQ ID No. 16:    TATGGCGACCGCAGGGAAGA
KWI-Dhalo 17: SEQ ID No. 17:    CTAATATATGCCGCCACGAA
KWI-Dhalo 18: SEQ ID No. 18:    TCACATAATTGCTGGGAGAA
KWI-Dhalo 19: SEQ ID No. 19:    CGCTTTATGGACGCTATGAA
KWI-Dhalo 20: SEQ ID No. 20:    CTCTATGCGAACCATGAATG
KWI-Dhalo 21: SEQ ID No. 21:    ATGAATTTGGTCACGCAGAT
KWI-Dhalo 22: SEQ ID No. 22:    ATCAAAACCACCAACTACCC
KWI-Dhalo 23: SEQ ID No. 23:    TGGGAGGGTACGCCTGAAGAGAACCTGTTA
KWI-Dhalo 24: SEQ ID No. 24:    TTCGGGGCTTCTTCCGTTGG
KWI-Dhalo 25: SEQ ID No. 25:    GCCATTAAGATAACGGATAA
KWI-Dhalo 26: SEQ ID No. 26:    CGTGAAGAAAATCTTCTATA
KWI-Dhalo 27: SEQ ID No. 27:    AAGCCCAGCCCTTTATCCTC
KWI-Dhalo 28: SEQ ID No. 28:    CCTTGGTATACGCTTAGAAA
KWI-Dhalo 29: SEQ ID No. 29:    TATGGCTGAATACATTGAAT
KWI-Dhalo 30: SEQ ID No. 30:    TTTGGTGGTGATGATAAGAT
KWI-Dhalo 31: SEQ ID No. 31:    GTGGTGCCCAATGCTCTAGA
KWI-Dhalo 32: SEQ ID No. 32:    TGAGAAACGCTTTAAGTATG
KWI-Dhalo 33: SEQ ID No. 33:    CCTTGGGGAACAATCACGCG
KWI-Dhalo 34: SEQ ID No. 34:    GCTCTAACACCAAGGGTTCCCTA
KWI-Dhalo 35: SEQ ID No. 35:    AGGATGCTTACCGACCTGCCCCTTG
KWI-Dhalo 36: SEQ ID No. 36:    CGGTATCCGTGAGTTCTGTA
KWI-Dhalo 37: SEQ ID No. 37:    AGACCTGCGGCATCTGTGCC
KWI-Dhalo 38: SEQ ID No. 38:    TTGTCCTACCCAAGCTATCTCGC
KWI-Dhalo 39: SEQ ID No. 39:    CTATGACTCACCCTACTGGG
KWI-Dhalo 40: SEQ ID No. 40:    ATAACGTCAGCGGCTATGAG
KWI-Dhalo 41: SEQ ID No. 41:    TACCAACTGTGAGACCTTCT
KWI-Dhalo 42: SEQ ID No. 42:    CCTTCTTCACTATGAGCAAT
KWI-Dhalo 43: SEQ ID No. 43:    AACTCCTGGGTGCACAACTT
KWI-Dhalo 44: SEQ ID No. 44:    GGTCAAGTCCACTGTTGCCA
KWI-Dhalo 45: SEQ ID No. 45:    CTACGCCCGTTTTTAACGGT
KWI-Dhalo 46: SEQ ID No. 46:    GCTACTCACCAAGCAGGGATGA
```

EXAMPLE 1-2

100 grams of a soil polluted by cis-dichloroethylene (DCE) and 50 milliliters of an underground water were placed in a 150 ml vial, whereto lactic acid was added in an amount sufficient to bring about a concentration of 100 mg/l, whereupon the vial was plugged by a butyl rubber stopper and was sealed with an aluminum cap. Two vials were used, for which the same procedures as above were carried out. One of the vials was inoculated with a bacterial suspension, from which the chlorinated ethylene-decomposing gene had been detected, in such an amount that the concentration of the chlorinated ethylene-decomposing gene will finally be $2.5 \times 10^4$ copies per milliliter. The other vial was used as a control without any inoculation. The two vials were subjected to a stationary cultivation at 30° C., while taking a sample for each at a regular interval.

In order to detect the chlorinated ethylene-decomposing gene, two nucleotides each having a base sequence complementary either to KWI-Dhalo 5 or to KWI-Dhalo 20, respectively, were used as the primer pair. For the detection, LightCycler (trademark, a product of K.K. Diagnostic) was used. For the PCR, a kit of LightCycler DNA MASTER SYBR GREEN I (trademark) was employed. The reaction condition was as recited in Table 2.

TABLE 2

| Segment | Target temp. (° C.) | Time maintained (sec) | Rate of temp. variation(° C./sec) | Fluorescence detected |
|---|---|---|---|---|
| Denaturation | | | | |
| Number of cycle = 1 | | | | |
| 1 | 95 | 120 | 20 | none |
| Quantitative analysis | | | | |
| Number of cycle = 50(segment 1 -> 2 -> 3 -> back to 1) | | | | |
| 1 | 95 | 0 | 20 | none |
| 2 | 53 | 15 | 20 | none |
| 3 | 72 | 30 | 2 | detected once |
| Thawing | | | | |
| Number of cycle = 1 | | | | |
| 1 | 95 | 0 | 20 | none |
| 2 | 63 | 10 | 20 | none |
| 3 | 85 | 0 | 0.2 | detected continuously |
| Cooling | | | | |
| Number of cycle = 1 | | | | |
| 1 | 40 | 30 | 20 | none |

Variation of the concentration of cis-DCE in the vial inoculated with the bacterial suspension, from which the chlorinated ethylene-decomposing gene had been detected, in the course of cultivation is shown in FIG. 1. As seen, the decomposition of the chlorinated ethylene became remarkable after about 20 days from the start of the experiment, while at the same time vinyl chloride (VC) became to be detected. Thereafter, VC was also decomposed and, after about 135 days, it was converted completely into ethylene.

Figure 2:
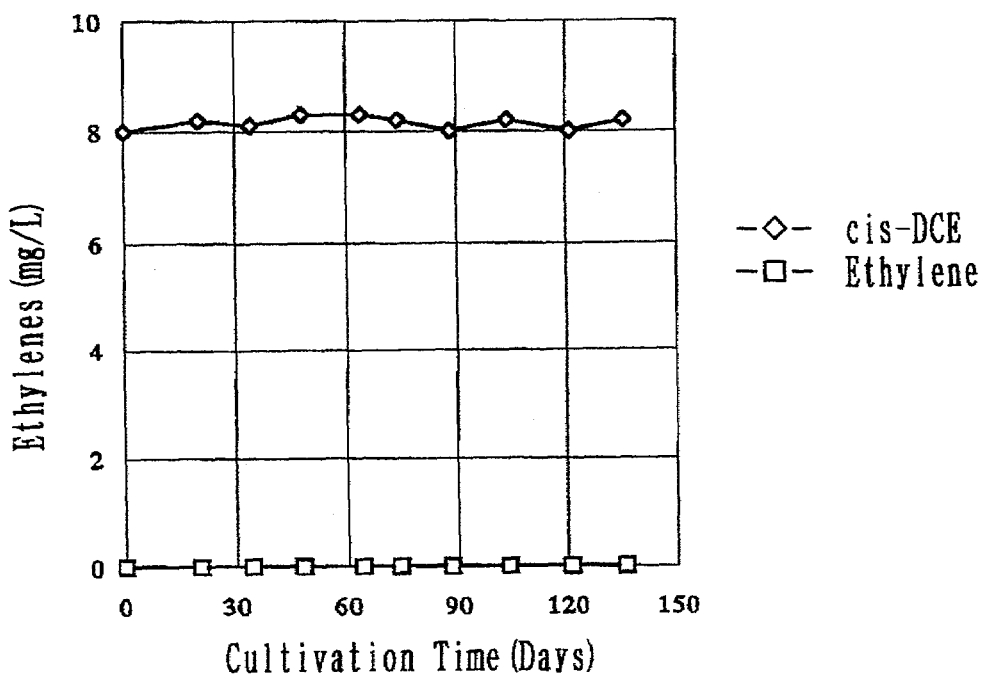
FIG. 2 is a graph showing the results of the control experiment of Example 1-2.

On the other hand, no cis-DCE was detected in the control during this period, as seen in FIG. 2.

From the above, it is seen that addition of a liquor, from which chlorinated ethylene-decomposing bacterium has been detected, to a polluted environment has an effect of accelerating decomposition of chlorinated ethylene.

EXAMPLE 1-3

Wells were settled at two positions (point A and point B) apart from each other at a distance of 1 meter on the ground polluted by chlorinated ethylene. Underground water was pumped up from the point B at a rate of 3 liters per minute, which was introduced into the well of point A. On the introduction of water into the well of point A, lactic acid was added to the water at a rate of 100 mg per liter. The polluted aquifer in this area was at a depth of 3 meters beneath the ground surface with an aquifer thickness of 4 meters.

Figure 3:
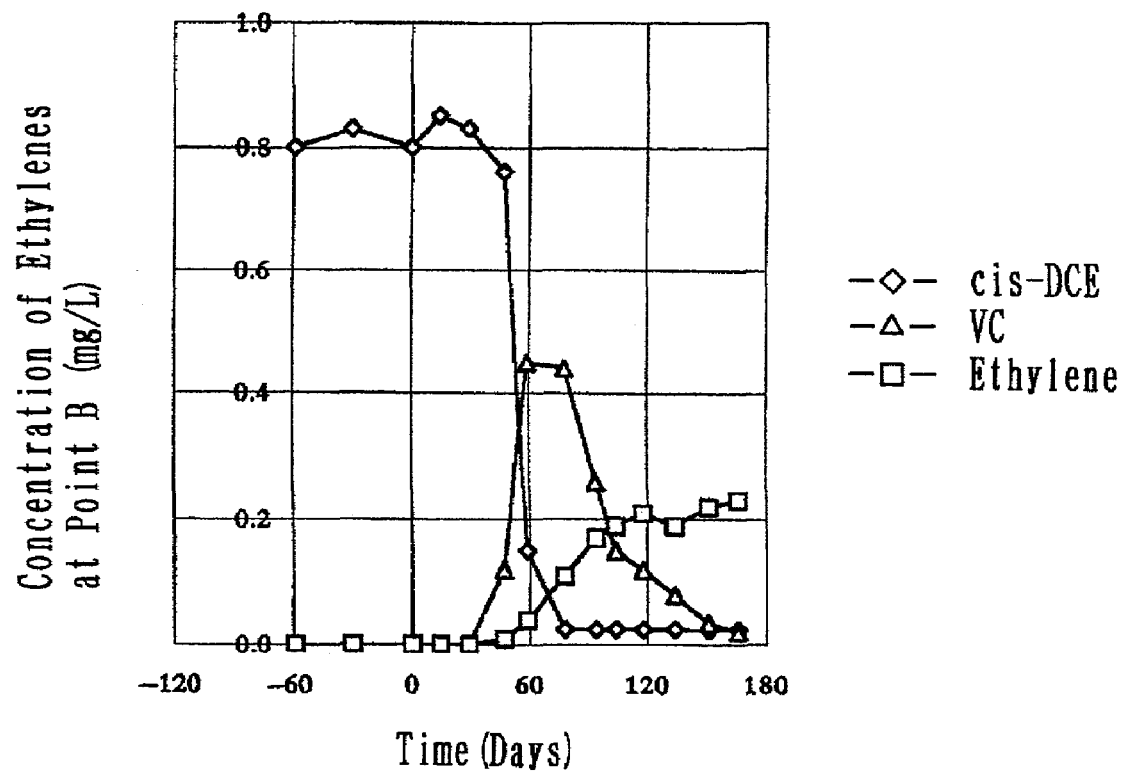
FIG. 3 is a graph showing the experimental results of Example 1-3.

The underground water was sampled at a regular interval at the point B to determine the concentrations of the ethylenic compounds (ethylenes). The results are shown in FIG. 3. In FIG. 3, the abscissa indicates the elapsed time and the origin refers to the point of time at which 50 liters of the bacterial suspension (with a gene concentration of $2.6 \times 10^6$ copies per milliliter) of the chlorinated ethylene-decomposing bacterium detected had been introduced into the well at the point B. Before the introduction of the bacterial suspension, no decomposition of dichloroethylene occurred, whereas decomposition thereof became marked after 20 days from the start of the introduction and 100% ethylenization was reached after about 170 days from the start of the introduction.

From the above, it is seen that introduction of a liquor, from which chlorinated ethylene-decomposing bacterium has been detected, will have an effect of accelerating decomposition of chlorinated ethylene also in the field.

REFERENCE EXAMPLE 2-1

In a batch-wise test of dechlorination using dechlorination bacteria, four vials among eight vials which have been confirmed that cis-1,2-dichloroethylene in these vials was decomposed showed prompt decomposition of vinyl chloride under 100% conversion into ethylene, while the remaining four vials showed that vinyl chloride was decomposed partly but a considerable part thereof remained undecomposed. DNAs were extracted from these eight vials, for which PCR synthesis of DNA fragments including the entire range of the gene tceA was attempted. The primer pair employed here (5'-TAACCTTCTAAAACATCCTG-3' (SEQ ID No.: 48) and 5'-GCACCACCCATAATAATCTA-3') (SEQ ID No.: 49) was designed from the sequence data of AF228507 registered in the GenBank in USA, wherein an adjoining region of the chlorinated ethylene-decomposing gene was utilized. The base sequence data of AF228507 include the chlorinated ethylene-decomposing gene tceA registered.

By the PCR synthesis, clones which have high homologies with respect to the base arrangement of the chlorinated ethylene-decomposing gene tceA were obtained from eight vials, of which base sequences were determined. The base sequence for the chlorinated ethylene-decomposing gene was the same for all the eight samples and had a homology of 96% with respect to the base arrangement of the gene tceA of the above-mentioned AF228507. The determined entire base sequence of the chlorinated ethylene-decomposing gene is recited in SEQ ID No. 68 in the SEQUENCE LISTING.

EXAMPLE 2-1

The base sequence in the region from the 1st to the 500th base upstream of the chlorinated ethylene-decomposing gene (gene tceA) was determined by using the PCR-synthesized fragments of Reference Example 2-1. From this, the base sequence as given in SEQ ID No. 64 was determined for four vials containing a vinyl chloride-decomposing bacterium of high activity. For the remaining four vials containing a vinyl chloride-decomposing bacterium of lower activity, the base sequence given in SEQ ID No. 65 was determined. The base sequence of SEQ ID No. 65 was in coincidence with the base sequence data of AF228507 including the gene tceA of the bacterium *Dehalococcoides ethenogens* 195 in the corresponding portion. The difference between the base sequences of SEQ ID No. 64 and SEQ ID No. 65 is as shown in the sequence diagrams (2) and (3).

EXAMPLE 2-2

Samples of underground waters were collected from the three locations A, B and C, where the ethylenization proceeded fairly, and from the three other locations D, E and F, where decomposition of vinyl chloride was quite slow and accumulation of vinyl chloride was recognized. DNA extraction was carried out from each 100 ml of these underground waters in the manner as given below:

(1) Extraction of DNA

Each 100 ml of each underground water were filtered through a filter of a pore size of 0.2 μm and were stored in a tube of a capacity of 2 ml. To the tube were added then 1 ml of zirconia/silica beads of 0.1 mm bead size and 1 ml of an extraction buffer {100 mM Tris-HCl (pH=8.0), 100 mM sodium EDTA (pH=8.0), 100 mM sodium phosphate (pH=8.0) and 1.5 M NaCl}, whereupon the mixture was treated in a cell crusher "Bead Beater" for 2 minutes. The so-treated mixture was then subjected to three repeats of freezing/thawing and, then, 10 μl of proteinase K (10 mg/ml) were added to the mixture and the resulting mixture was held at 37° C. thermostatically for 30 minutes. To this mixture were then added 250 μl of 10% SDS solution and the resulting mixture was held thermostatically at 65° C. for two hours, whereupon the mixture was subjected again to the above-mentioned Bead Beater treatment. Then, the treated mixture was centrifuged at 8000×g for 10 minutes at room temperature and the resulting supernatant was collected. The supernatant was treated with chloroform to remove contamination proteins, whereupon the separated upper aqueous layer was isolated and processed by addition of an equal volume of isopropanol, allowed to stand for 60 minutes at room temperature and centrifugation at 8000×g for 20 minutes at room temperature to precipitate the DNA. The resulting precipitate was washed with 70% ethanol and then dried, before it was re-dissolved in 50 μl of sterile distilled water.

Using this extracted DNA solution, PCR was performed in the manner as described below, in order to examine whether or not high performance vinyl chloride-decomposing bacterium was present.

(2) Confirmation of presence of high performance vinyl chloride-decomposing bacterium by PCR Using 1 μl of the extracted DNA solution obtained in the above (1) as the template, the region of the gene tceA was amplified by PCR. The volume of the reaction liquor of PCR-amplification was supplemented to 100 μl and there were used 2.5 U of Ex Taq DNA polymerase (a product of Takara Shuzo Co., Ltd.) and 200 μM of dNTP. For the primer pair, a combination of KWI-VC 5 (5'-CTTCCCT-TAAGATAGCATCA-3') (SEQ ID No. 54) and VCr 1 (5'-CGCCTTGTGACTGTAGAATG-3') (SEQ ID No. 69), each 20 pmol for each component, was used. KWI-VC 5 used here is the nucleic acid of SEQ ID No. 54. For other components of the reaction liquor composition, the guides of the manual attached to the PCR kit were followed. The PCR was effected according to the steps which comprise pre-heating at 94° C. for 2 minutes, subsequent 35 cyclic repeats of the first step of 94° C. for 20 seconds, the second step of 50° C. for 30 seconds and the third step of 72° C. for 30 seconds, followed by a post-extension of 72° C. for 7 minutes.

Each 2 μl of the PCR reaction liquor were subjected to an agarose electrophoresis, wherein presence of a high performance vinyl chloride-decomposing bacterium was judged when a DNA fragment of expected size (145 bp) was synthesized. From this, synthesis of the DNA fragment was confirmed for the underground water samples from the locations A, B and C, while such DNA synthesis was not recognized for the underground water samples from the locations D, E and F. From this result, it was shown that detection of a high performance vinyl chloride-decomposing bacterium can be attained by the use of the nucleic acids according to the present invention.

The invention claimed is:

1. A method for detecting dechlorination bacteria, comprising:

performing a polymerase chain reaction using a nucleic acid selected from SEQ ID No.: 1 through SEQ ID No.: 46 which hybridizes with the DNA of dechlorination bacteria at chlorinated ethylene-decomposing gene tceA of SEQ ID No.: 47 or with SEQ ID No.: 64 located upstream of the gene tceA for the primer and using nucleic acid present in a sample bacterium for the template and detecting the synthesized DNA fragments to determine if dechlorination bacteria is present.

2. A method for detecting dechlorination bacteria, comprising:

forming a labeled probe made up of a label and the nucleic acid selected from the sequences of SEQ ID No.: 1 through SEQ ID No.: 46 which hybridizes with the DNA of dechlorination bacteria at chlorinated ethylene-decomposing gene tceA of SEQ ID No.: 47 or with SEQ ID No.: 64 located upstream of the gene;

bringing the labeled probe into contact with a sample bacterium or nucleic acid from the sample bacterium to effect an RNA- or DNA-hybridization and detecting the label of the probe to determine if dechlorination bacteria is present.

* * * * *

SEQUENCE LISTING

```
<160> NUMBER OF SEQ ID NOS: 68

<210> SEQ ID NO 1
<211> LENGTH: 17
<212> TYPE: DNA
<213> ORGANISM: Artificial Sequence
<220> FEATURE:
<222> LOCATION: (1)...(17)
<223> OTHER INFORMATION: primer

<400> SEQUENCE: 1
gaggctaggt ttggcag                                                    17

<210> SEQ ID NO 2
<211> LENGTH: 17
<212> TYPE: DNA
<213> ORGANISM: Artificial Sequence
<220> FEATURE:
<222> LOCATION: (1)...(17)
<223> OTHER INFORMATION: primer

<400> SEQUENCE: 2
ttgcagagaa taacctg                                                    17

<210> SEQ ID NO 3
<211> LENGTH: 30
<212> TYPE: DNA
<213> ORGANISM: Artificial Sequence
```

```
<220> FEATURE:
<222> LOCATION: (1)...(30)
<223> OTHER INFORMATION: primer

<400> SEQUENCE: 3
ttaaagatgt tgatgacctg ctgtcagcag                              30

<210> SEQ ID NO 4
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 4
gtaaagcttt agagggtgac                                         20

<210> SEQ ID NO 5
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 5
gggtgaccac gctaataaag                                         20

<210> SEQ ID NO 6
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 6
tgagccatgg tgggttacca                                         20

<210> SEQ ID NO 7
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 7
tgaggatcca acctgtaata                                         20

<210> SEQ ID NO 8
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 8
gccttataaa aagatacagc                                         20

<210> SEQ ID NO 9
<211> LENGTH: 20
<212> TYPE: DNA
<213> ORGANISM: Artificial Sequence
<220> FEATURE:
```

```
<222> LOCATION: (1)...(20)
<223> OTHER INFORMATION: primer

<400> SEQUENCE: 9
tggaacaacc agggagcata                                                    20

<210> SEQ ID NO 10
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 10
cttcttacct gaggattacc                                                    20

<210> SEQ ID NO 11
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 11
tgtctccaac ctatacaggt                                                    20

<210> SEQ ID NO 12
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 12
atactgcgat agtgccttta                                                    20

<210> SEQ ID NO 13
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 13
taaaatcagg catagactgg                                                    20

<210> SEQ ID NO 14
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 14
atgaaggaaa atattgatcc                                                    20

<210> SEQ ID NO 15
<211> LENGTH: 20
<212> TYPE: DNA
<213> ORGANISM: Artificial Sequence
<220> FEATURE:
<222> LOCATION: (1)...(20)
```

```
<223> OTHER INFORMATION: primer

<400> SEQUENCE: 15
agattatgac cctggtgaac                                                 20

<210> SEQ ID NO 16
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 16
tatggcgacc gcagggaaga                                                 20

<210> SEQ ID NO 17
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 17
ctaatatatg ccgccacgaa                                                 20

<210> SEQ ID NO 18
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 18
tcacataatt gctgggagaa                                                 20

<210> SEQ ID NO 19
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 19
cgctttatgg acgctatgaa                                                 20

<210> SEQ ID NO 20
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 20
ctctatgcga accatgaatg                                                 20

<210> SEQ ID NO 21
<211> LENGTH: 20
<212> TYPE: DNA
<213> ORGANISM: Artificial Sequence
<220> FEATURE:
<222> LOCATION: (1)...(20)
<223> OTHER INFORMATION: primer
```

```
<400> SEQUENCE: 21
atgaatttgg tcacgcagat                                              20

<210> SEQ ID NO 22
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 22
atcaaaacca ccaactaccc                                              20

<210> SEQ ID NO 23
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 23
tgggagggta cgcctgaaga gaacctgtta                                   30

<210> SEQ ID NO 24
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 24
ttcggggctt cttccgttgg                                              20

<210> SEQ ID NO 25
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 25
gccattaaga taacggataa                                              20

<210> SEQ ID NO 26
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 26
cgtgaagaaa atcttctata                                              20

<210> SEQ ID NO 27
<211> LENGTH: 20
<212> TYPE: DNA
<213> ORGANISM: Artificial Sequence
<220> FEATURE:
<222> LOCATION: (1)...(20)
<223> OTHER INFORMATION: primer
```

-continued

```
<400> SEQUENCE: 27
aagcccagcc ctttatcctc                                              20

<210> SEQ ID NO 28
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 28
ccttggtata cgcttagaaa                                              20

<210> SEQ ID NO 29
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 29
tatggctgaa tacattgaat                                              20

<210> SEQ ID NO 30
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 30
tttggtggtg atgataagat                                              20

<210> SEQ ID NO 31
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 31
gtggtgccca atgctctaga                                              20

<210> SEQ ID NO 32
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 32
tgagaaacgc tttaagtatg                                              20

<210> SEQ ID NO 33
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 33
```
ccttggggaa caatcacgcg                                                    20

<210> SEQ ID NO 34
<211> LENGTH: 23
<212> TYPE: DNA
<213> ORGANISM: Artificial Sequence
<220> FEATURE:
<222> LOCATION: (1)...(23)
<223> OTHER INFORMATION: primer

<400> SEQUENCE: 34
gctctaacac caagggttcc cta                                                23

<210> SEQ ID NO 35
<211> LENGTH: 25
<212> TYPE: DNA
<213> ORGANISM: Artificial Sequence
<220> FEATURE:
<222> LOCATION: (1)...(25)
<223> OTHER INFORMATION: primer

<400> SEQUENCE: 35
aggatgctta ccgacctgcc ccttg                                              25

<210> SEQ ID NO 36
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 36
cggtatccgt gagttctgta                                                    20

<210> SEQ ID NO 37
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 37
agacctgcgg catctgtgcc                                                    20

<210> SEQ ID NO 38
<211> LENGTH: 23
<212> TYPE: DNA
<213> ORGANISM: Artificial Sequence
<220> FEATURE:
<222> LOCATION: (1)...(23)
<223> OTHER INFORMATION: primer

<400> SEQUENCE: 38
ttgtcctacc caagctatct cgc                                                23

<210> SEQ ID NO 39
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 39

```
ctatgactca ccctactggg                                              20
```

<210> SEQ ID NO 40
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 40

```
ataacgtcag cggctatgag                                              20
```

<210> SEQ ID NO 41
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 41

```
taccaactgt gagaccttct                                              20
```

<210> SEQ ID NO 42
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 42

```
ccttcttcac tatgagcaat                                              20
```

<210> SEQ ID NO 43
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 43

```
aactcctggg tgcacaactt                                              20
```

<210> SEQ ID NO 44
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 44

```
ggtcaagtcc actgttgcca                                              20
```

<210> SEQ ID NO 45
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 45

```
ctacgcccgt ttttaacggt                                              20
```

-continued

<210> SEQ ID NO 46
<211> LENGTH: 22
<212> TYPE: DNA
<213> ORGANISM: Artificial Sequence
<220> FEATURE:
<222> LOCATION: (1)...(22)
<223> OTHER INFORMATION: primer

<400> SEQUENCE: 46
gctactcacc aagcagggat ga                                           22

<210> SEQ ID NO 47
<211> LENGTH: 1665
<212> TYPE: DNA
<213> ORGANISM: Unknown
<220> FEATURE:
<222> LOCATION: (1)...(1665)
<223> OTHER INFORMATION: A gene for degrading chlorinated ethylene.

<400> SEQUENCE: 47
atgagtgaaa aatatcattc tacagtcaca aggcgtgatt tcatgaagag gctaggtttg      60
gcaggagccg gtgcgggggc actgggtgcc gctgtacttg cagagaataa cctgccgcat    120
gagtttaaag atgttgatga cctgctgtca gcaggtaaag cttttagaggg tgaccacgct    180 aataaagtaa acaatgagcc atggtgggtt accacgcgtg atcatgagga tccaacctgt    240
aatatagatt ggagccttat aaaaagatac agcggttgga caaccaggg agcatacttc     300 ttacctgagg attacctgtc tccaacctat acaggtagaa gacatactat tgttgattca    360
tctctagaag taaaattaca gggtaaaaaa tactgcgata gtgcctttat aaaatcaggc    420
atagactgga tgaaggaaaa tattgatcca gattatgacc ctggtgaact gggctatggc    480
gaccgcaggg aagatgccct aatatatgcc gccacgaatg gctcacataa ttgctgggag    540
aacccgcttt atggacgcta tgaaggttct aggccttatc tctctatgcg aaccatgaat    600
ggaataaacg gcttgcatga atttggtcac gcagatatca aaaccaccaa ctacccgaag    660
tgggagggta cgcctgaaga gaacctgtta atcatgcgca ccgccgcgcg ctacttcggg    720
gcttcttccg ttggcgccat taagataacg gataacgtga agaaaatctt ctataccaaa    780
gcccagccct ttatcctcgg gccttggtat acgcttagaa atatggctga atacattgaa    840
tatccggtcc cagtagataa ttatgctata cccattgtgt ttgaagatgt tcctgcagac    900
cagggacact acagctacaa gcgctttggt ggtgatgata agatagtggt gcccaatgct    960
ctagagaata tcttcaccta tactatcatg ctccctgaga aacgctttaa gtatgcacat   1020
agcgtaccta tggacccatg ctcttgtatt gcctatcccc tctttacaga ggctgaggca   1080
cgcattcagc acttcattgc aggccttggt tataactcaa tgggtggcgg agttgaagct   1140
tggggtccgg gcggtgcctt cggcaactta agtggccttg ggaacaatc acgcgtatca   1200 agcattattg agccccgcta cggctctaac accaagggtt ccctaaggat gcttaccgac   1260 ctgcccttg cccccaccaa gcctatagat gccggtatcc gtgagttctg taagacctgc   1320
ggcatctgtg ccgagcattg tcctacccaa gctatctcgc atgaagggcc gcgctatgac   1380
tcaccctact gggataacgt cagcggctat gagggctggc accttgacta tcataagtgc   1440
attaactgta ccaactgtga gaccttctgc cccttcttca ctatgagcaa taactcctgg   1500
gtgcacaact tggtcaagtc cactgttgcc actacgcccg ttttaacgg tttctttaag   1560 aatatggaag aagccttcgg ctacggcccg cgctactcac caagcaggga tgaatggtgg   1620
gcctcagaaa acccaatacg cggcgcaagc gtagatattt tttaa          1665

<210> SEQ ID NO 48
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 48
taaccttcta aaacatcctg          20

<210> SEQ ID NO 49
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 49
gcaccaccca taataatcta          20

<210> SEQ ID NO 50
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 50
atgtttgaaa ttccgcattg          20

<210> SEQ ID NO 51
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 51
tctccaacta actcgctttg tgactattat          30

<210> SEQ ID NO 52
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 52 taaacttta atattttttt ttcattcttt          30

<210> SEQ ID NO 53
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 53
ttccaaagtg ctatcttcta cttaacaacc          30

<210> SEQ ID NO 54
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 54
cttcccttaa gatagcatca                                         20

<210> SEQ ID NO 55
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 55
aggaggcaga ttatgcgtat tggcttgcgg                              30

<210> SEQ ID NO 56
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 56
gaaaagcttt ttttaatgag gtattttaaa                              30

<210> SEQ ID NO 57
<211> LENGTH: 20
<212> TYPE: DNA
<213> ORGANISM: Artificial Sequence
<220> FEATURE:
<222> LOCATION: (1)...(20)
<223> OTHER INFORMATION: primer

<400> SEQUENCE: 57
atatttgtag tttcgcattg                                         20

<210> SEQ ID NO 58
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 58
tctccaacta actcgttttg tgactattat                              30

<210> SEQ ID NO 59
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 59
taaactttta atattgtttt ttcattcttt                              30

<210> SEQ ID NO 60
<211> LENGTH: 30
<212> TYPE: DNA
<213> ORGANISM: Artificial Sequence
<220> FEATURE:
<222> LOCATION: (1)...(30)
<223> OTHER INFORMATION: primer

<400> SEQUENCE: 60
ttccaaggtg ctatcttcta cttaacaaac                                      30

<210> SEQ ID NO 61
<211> LENGTH: 23
<212> TYPE: DNA
<213> ORGANISM: Artificial Sequence
<220> FEATURE:
<222> LOCATION: (1)...(23)
<223> OTHER INFORMATION: primer

<400> SEQUENCE: 61
cttcccgttg agtaaacatt tca                                             23

<210> SEQ ID NO 62
<211> LENGTH: 31
<212> TYPE: DNA
<213> ORGANISM: Artificial Sequence
<220> FEATURE:
<222> LOCATION: (1)...(31)
<223> OTHER INFORMATION: primer

<400> SEQUENCE: 62
aggaggcatg ttatggatac ttggcttgcg g                                    31

<210> SEQ ID NO 63
<211> LENGTH: 31
<212> TYPE: DNA
<213> ORGANISM: Artificial Sequence
<220> FEATURE:
<222> LOCATION: (1)...(31)
<223> OTHER INFORMATION: primer

<400> SEQUENCE: 63
gaaaagcttt ttttaaatga ggtattttaa a                                    31

<210> SEQ ID NO 64
<211> LENGTH: 422
<212> TYPE: DNA
<213> ORGANISM: Unknown
<220> FEATURE:
<223> OTHER INFORMATION: Upstream sequence of tceA gene for degrading
      chlorinated ethylene.

<400> SEQUENCE: 64
atgtttgaaa ttccgcattg ctatggttcc aataagtgtt attatactca ttaatgagag      60
atttacatac tcttccccgt aggtattaat tctatcttcc tgctgcttaa tgttatttaa     120
atccatatca cgctcgtttc ccattttttta ctcacgtccc tcccaatcta attctccaac    180
taactcgctt tgtgactatt atattctaat ttaataaatt ttcaataaaa gttttagtaa     240
acttttaata ttttttttttc attctttcgt ggcacgtgcg ctttccaaag tgctatcttc    300
tacttaacaa cccttccctt aagatagcat caaggaggca gattatgcgt attggcttgc    360
ggactaccgc atgacagacg ccaaagtgcg aaaagctttt tttaatgagg tattttaaaa    420
gt                                                                   422

<210> SEQ ID NO 65
<211> LENGTH: 427
<212> TYPE: DNA
<213> ORGANISM: Dehalococcoides ethenogenes

<400> SEQUENCE: 65

| | | | | | |
|---|---|---|---|---|---|
| atatttgtag | tttcgcattg | ctatggttcc | aataagtgtt | attatactca | ttaatgagag | 60 |
| atttacatac | tcttccccgt | aggtattaat | tctatcttcc | tgctgcttaa | tgttatttaa | 120 |
| atccatatca | cgctcgtttc | cccattttta | ctcacgtccc | tcccaatcta | attctccaac | 180 |
| taactcgttt | tgtgactatt | atattctaat | ttaataaatt | ttcaataaaa | gttttagtaa | 240 |
| acttttaata | ttgttttttc | attctttcgt | ggcacgtgcg | ctttccaagg | tgctatcttc | 300 |
| tacttaacaa | accttcccgt | tgagtaaaca | tttcaaggag | gcatgttatg | gatacttggc | 360 |
| ttgcggacta | ccgcatgaca | gacgccaaag | tgcgaaaagc | ttttttttaaa | tgaggtattt | 420 |
| taaaagt | | | | | | 427 |

<210> SEQ ID NO 66
<211> LENGTH: 495
<212> TYPE: DNA
<213> ORGANISM: Unknown
<220> FEATURE:
<223> OTHER INFORMATION: Partial nucleotide sequence of TceA gene for
      degrading chlorinated ethylene and upstream sequence thereof.

<400> SEQUENCE: 66

| | | | | | |
|---|---|---|---|---|---|
| atgtttgaaa | ttccgcattg | ctatggttcc | aataagtgtt | attatactca | ttaatgagag | 60 |
| atttacatac | tcttccccgt | aggtattaat | tctatcttcc | tgctgcttaa | tgttatttaa | 120 |
| atccatatca | cgctcgtttc | cccattttta | ctcacgtccc | tcccaatcta | attctccaac | 180 |
| taactcgctt | tgtgactatt | atattctaat | ttaataaatt | ttcaataaaa | gttttagtaa | 240 |
| acttttaata | ttttttttttc | attctttcgt | ggcacgtgcg | ctttccaaag | tgctatcttc | 300 |
| tacttaacaa | cccttccctt | aagatagcat | caaggaggca | gattatgcgt | attggcttgc | 360 |
| ggactaccgc | atgacagacg | ccaaagtgcg | aaaagctttt | tttaatgagg | tattttaaaa | 420 |
| gtatgagtga | aaaatatcat | tctacagtca | caaggcgtga | tttcatgaag | aggctaggtt | 480 |
| tggcaggagc | cggtg | | | | | 495 |

<210> SEQ ID NO 67
<211> LENGTH: 500
<212> TYPE: DNA
<213> ORGANISM: Dehalococcoides ethenogenes

<400> SEQUENCE: 67

| | | | | | |
|---|---|---|---|---|---|
| atatttgtag | tttcgcattg | ctatggttcc | aataagtgtt | attatactca | ttaatgagag | 60 |
| atttacatac | tcttccccgt | aggtattaat | tctatcttcc | tgctgcttaa | tgttatttaa | 120 |
| atccatatca | cgctcgtttc | cccattttta | ctcacgtccc | tcccaatcta | attctccaac | 180 |
| taactcgttt | tgtgactatt | atattctaat | ttaataaatt | ttcaataaaa | gttttagtaa | 240 |
| acttttaata | ttgttttttc | attctttcgt | ggcacgtgcg | ctttccaagg | tgctatcttc | 300 |
| tacttaacaa | accttcccgt | tgagtaaaca | tttcaaggag | gcatgttatg | gatacttggc | 360 |
| ttgcggacta | ccgcatgaca | gacgccaaag | tgcgaaaagc | ttttttttaaa | tgaggtattt | 420 |
| taaaagtatg | agtgaaaaat | atcattctac | agtcacaagg | cgtgatttca | tgaagagatt | 480 |
| aggttttggca | ggagccggtg | | | | | 500 |

<210> SEQ ID NO 68
<211> LENGTH: 1665
<212> TYPE: DNA
<213> ORGANISM: Unknown
<220> FEATURE:
<222> LOCATION: (1)...(1665)
<223> OTHER INFORMATION: TceA gene for degrading chlorinated ethylene.

<400> SEQUENCE: 68

```
atgagtgaaa aatatcattc tacagtcaca aggcgtgatt tcatgaagag gctaggtttg      60
gcaggagccg gtgcgggggc actgggtgcc gctgtacttg cagagaataa cctgccgcat     120
gagtttaaag atgttgatga cctgctgtca gcaggtaaag ctttagaggg tgaccacgct     180
aataaagtaa acaatgagcc atggtgggtt accacgcgtg atcatgagga tccaacctgt     240
aatatagatt ggagccttat aaaaagatac agcggttgga caaccagggg agcatacttc     300
ttacctgagg attacctgtc tccaacctat acaggtagaa gacatactat tgttgattca     360
tctctagaag taaaattaca gggtaaaaaa tactgcgata gtgcctttat aaaatcaggc     420
atagactgga tgaaggaaaa tattgatcca gattatgacc ctggtgaact gggctatggc     480
gaccgcaggg aagatgccct aatatatgcc gccacgaatg gctcacataa ttgctgggag     540
aacccgcttt atggacgcta tgaaggttct aggccttatc tctctatgcg aaccatgaat     600
ggaataaacg gcttgcatga atttggtcac gcagatatca aaaccaccaa ctacccgaag     660
tgggagggta cgcctgaaga gaacctgtta atcatgcgca ccgccgcgcg ctacttcggg     720
gcttcttccg ttggcgccat taagataacg gataacgtga agaaaatctt ctataccaaa     780
gcccagccct ttatcctcgg gccttggtat acgcttagaa atatggctga atacattgaa     840
tatccggtcc cagtagataa ttatgctata cccattgtgt ttgaagatgt tcctgcagac     900
cagggacact acagctacaa gcgctttggt ggtgatgata agatagtggt gcccaatgct     960
ctagagaata tcttcaccta tactatcatg ctccctgaga aacgctttaa gtatgcacat    1020
agcgtaccta tggacccatg ctcttgtatt gcctatcccc tctttacaga ggctgaggca    1080
cgcattcagc acttcattgc aggccttggt tataactcaa tgggtggcgg agttgaagct    1140
tggggtccgg gcggtgcctt cggcaactta agtggccttg ggaacaatc acgcgtatca     1200
agcattattg agccccgcta cggctctaac accaagggtt ccctaaggat gcttaccgac    1260
ctgccccttg cccccaccaa gcctatagat gccggtatcc gtgagttctg taagacctgc    1320
ggcatctgtg ccgagcattg tcctacccaa gctatctcgc atgaagggcc gcgctatgac    1380
tcaccctact gggataacgt cagcggctat gagggctggc accttgacta tcataagtgc    1440
attaactgta ccaactgtga gaccttctgc cccttcttca ctatgagcaa taactcctgg    1500
gtgcacaact tggtcaagtc cactgttgcc actacgcccg tttttaacgg tttctttaag    1560
aatatggaag aagccttcgg ctacggcccg cgctactcac caagcaggga tgaatggtgg    1620
gcctcagaaa acccaatacg cggcgcaagc gtagatattt tttaa                    1665
```